United States Patent [19]

MacLennan et al.

[11] 4,265,915

[45] May 5, 1981

[54] PROTEIN-CONTAINING FOOD MATERIAL

[76] Inventors: Mary E. MacLennan; Martial Lawson, both of 198 Parkes St., Helensburgh, New South Wales 2508, Australia

[21] Appl. No.: 957,380

[22] Filed: Nov. 3, 1978

[30] Foreign Application Priority Data

Nov. 8, 1977 [AU] Australia ............................. PD2345

[51] Int. Cl.$^3$ ......................... A23J 1/12; C12D 13/06
[52] U.S. Cl. ........................................ 426/28; 426/18; 426/44; 426/46; 426/48; 426/52; 426/574; 426/656; 426/802; 435/68; 435/913; 435/933; 435/929; 435/939
[58] Field of Search .................. 426/18, 574, 802, 44, 426/46, 48, 49, 52; 435/254, 68, 913, 933, 929, 939

[56] References Cited

U.S. PATENT DOCUMENTS

| | | | |
|---|---|---|---|
| 2,885,048 | 5/1975 | Liggett | 426/18 |
| 3,151,038 | 9/1964 | Gray | 435/254 |
| 3,243,301 | 3/1966 | Hesseltine et al. | 426/46 |
| 3,809,614 | 5/1974 | Forss et al. | 435/254 |
| 3,829,363 | 8/1974 | Rogers et al. | 435/254 |
| 3,865,951 | 2/1975 | Spicer | 426/60 |
| 3,937,654 | 2/1976 | Solomons et al. | 435/254 |

FOREIGN PATENT DOCUMENTS

1277002 6/1972 United Kingdom .
1510012 5/1978 United Kingdom .

OTHER PUBLICATIONS

Trevelyan, W. E., (1974), Tropical Science, 16, pp. 179–194.
Martinelli, *Tempeh Fermentation : Package and Tray Fermentations,* Food Technology, vol. 18, pp. 167–171, 1964.
Hesseltine et al., (1967), Developments in Industrial Microbiology, 8, Chapter 20, pp. 179–186.

*Primary Examiner*—Joseph M. Golian
*Assistant Examiner*—Elizabeth A. Hatcher

[57] ABSTRACT

A process for the preparation of a textured protein-containing material in which an amylolytic fungus is grown on a moist starch based substrate which includes a nitrogen source assimilable by the fungus the substrate being provided in the form of small, partially gelatinized particles. During growth, the fungus degrades and utilizes a large proportion of the starch, resulting in a dense matrix of closely interwoven mycelia, randomly dispersed with substances containing the residual starch or starch degradation products. On the denaturation of the fungal mycelium, the product assumes a tough but resilient texture and when diced or minced has a similar appearance to meat.

29 Claims, No Drawings

PROTEIN-CONTAINING FOOD MATERIAL

This invention relates to a textured protein-containing fermented food material which can be used as an extender of, substitute for, or alternative to, meat.

Animal meat is considered a highly desirable component of the diet in many parts of the world, not only for its nutritional value but also because of its attractive texture and flavour properties. However, due to increasing costs and inherent inefficiencies of meat production, the search for protein-containing products which will substitute for, extend or provide an alternative to meat is becoming increasingly widespread. Probably the most difficult problem being encountered is simulation of the texture of natural meat.

Two basic techniques are used for imparting meat-like textures to vegetable protein preparations. The most common involves the moist extrusion at elevated temperatures and pressures of protein-containing meals or concentrates thereof, texturization resulting from the change in physical structure as the material passes through the extruder die to conditions of lower temperature and pressure. Depending on the protein source and conditions used, textured products of various types can be produced; however, few if any simulate meat in all important aspects. The second and more sophisticated technique involves the spinning of viscous protein preparations in a similar way to that used in producing synthetic textile fibres, the protein fibres being bundles together to produce material of fibrous texture. Products produced in this way more closely resemble meat but at present show little cost advantage over the natural products.

A number of methods are known for producing proteinaceous foods by fungal fermentation. A typical example of such processes is the preparation of the Indonesian fermented food, tempeh. Traditionally tempeh is prepared by the fermentation by species of Rhizopus, of dehulled soybeans in the form of a moist, solid substrate for a period of 24–36 hours. The traditional tempeh is prepared using unbroken halves of beans, although soybean grits have been used with similar results (Martinelli, A. & Hesseltine, C. W., Food Technol, 18, 167, 1964). After fermentation the beans or grits are bound by the fungal mycelium to give a product of firm, cheese-like consistency, in which the substrate particles are clearly visible and contribute significantly to the appearance and texture. This material is usually sliced and deep fried for consumption but is sometimes boiled in soups. The fried product resembles potato chips in consistency and flavour. The boiled product retains its cheese-like consistency and does not resemble meat in appearance or texture, due to the predominance of the soybean particles.

Similar products based on fungal fermentation of cereals or mixtures of cereals and soybeans have been described (Hesseltine, C. W. U.S. Pat. No. 3,243,801; (1967); Dev. Ind. Microbial. 8, 179). However, they do not possess the tough, fibrous, chewy texture associated with animal meats, and feature a predominance of residual substrate particles.

A process for producing simulated meat, fish and dairy products by fungal fermentation of vegetable raw materials is described by Liggett (U.S. Pat. No. 3,885,048) in which soybeans and grains are fermented in a similar manner to that described by Hesseltine, and the product combined with other ingredients in a novel manner to produce simulated meat products. One such fermented material is described as having the appearance, texture and flavour of a ground beef patty. Reproduction of this work by the present authors yielded a product which we consider to be clearly distinguishable from meat patties due to the visible presence of large particles of soybeans in the product. Such a product could not be used in mince form as the larger particles present would tend to fall out.

Other similar food products produced by fermentation of moist solid starch-based substrates by Rhizopus sp. have been described (Stanton W. R. & Wallbridge, A. J., British Pat. No. 1,277,002; Trevelyan, W. C., Tropical Science (1974) 16, p179). These substrates included an added source of non-protein nitrogen and other nutrients, in order to increase the protein content of the fermented product by conversion of the non-protein nitrogen to fungal protein. Most of the work relates to fermentation of cassava flour and similar starch sources, extruded into spaghetti-like rods of 3–5 mm diameter before fermentation. The products obtained after fermentation were of firm cheese-like consistency, and were cooked in a similar fashion to tempeh. Products produced in our laboratories according to the described methods did not possess a visual or textural resemblance to meat, due mainly to the predominance of large particles of unfermented substrate remaining in the fermented product.

The present invention relates to a textured protein-containing foodstuff which is produced by a fungal fermentation process and which has a texture and appearance such that it can be used as an extender or substitute for or alternative to meat in certain conformations, such as when minced or diced. The foodstuff derives from the ability of filamentous fungi when grown under suitable conditions on a moist solid fermentable starch-based substrate, to convert a large part of the starch to protein-containing fungal mycelium, which forms a dense closely interwoven hyphal matrix throughout the material entwining and binding together the residual components of the starch-depleted substrate. On appropriate denaturation of the protein-containing mycelium, for example by boiling the fermented material, the latter develops into a firm elastic substance which when cubed or minced has a marked resemblance to meat in texture and appearance.

It is believed that the resilient texture and meat like appearance of the product is due to the closely interwoven distribution of the mycelia and the substantial absence of large non-mycelial particles in the material.

According to the present invention, there is provided a process for preparing a protein-containing product, said process comprising the steps of:

(a) providing a particulate starch-based material which does or does not include a nitrogen source;

(b) partially gelatinising the starch component of said material in the presence of water to a particular substrate, composed of particles having all overall dimensions less than 3 mm (as hereinafter defined);

(c) adding a nitrogen source if, the nitrogen source in step (a) is absent or insufficient, before, during or after step (b) whilst maintaining the physical state of said substrate;

(d) inoculating said substrate with at least one amylolytic fungal strain;

(e) incubating said inoculated substrate in the presence of oxygen and moisture until substantially all particles of said substrate and/or degradation products thereof are closely bound by a network of mycelia; and (f) denaturing the products of step (e) wherein said nitrogen source is assimilable by said fungal strain(s), and is present in a total amount which is non-inhibitory and sufficient to allow adequate mycelial growth in step (e), and if said nitrogen source is particulate, the particles of said nitrogen source have all overall dimensions less than 2.5 mm (as hereinafter defined).

In another broad form the invention provides a protein-containing textured product comprising denatured fungal mycelia interwoven around and through one or more of starch, starch degradation products, moisture and gas bubbles and wherein substantially all maximum dimensions of major interhypal distances (as herein defined) do not exceed 3 mm, preferably 2 mm and more preferably 1 mm.

It has been found that the production of a product with meat-like appearance and texture requires observance of the following critical criteria.

1. The substrate must be provided in a physical and chemical form which will enable the fungus to degrade a large proportion of the solid starch-containing component, thereby nearly eliminating the presence of solid non-mycelial particles, which confer a spongy elastic texture to the final product. This is achieved by careful control of the particle of size of the starch-containing component so that no overall dimension exceeds 3 mm, preferably 2.0 mm, more preferably 1.0 mm; and by preparation of the substrate such that added water is absorbed uniformly and fully penetrates the starch-containing particles, preferably by thorough cooking.

2. A heavy fungal growth must be achieved forming a dense matrix of fungal mycelium throughout the product to entwine and tightly bind together the residual material. Some problems exist in definition of the proportion of fungal mycelium in a product in which the mycelium is integrally bound with other substrate components. Common methods of measuring cell mass, such as by measuring protein nitrogen cannot be used when protein is already present in the substrate. It has been found that an approximate indication of fungal mass can be achieved by measuring nucleic acid levels in the material using an appropriate method such as that of K. Burton (1956) Biochem. J. 62, 315–322.

It must be appreciated that the nucleic acid content varies between different micro-organisms, and within the same micro-organism when grown under different conditions, and at different stages of growth. However a reasonable approximation of mycelial content of the product can be obtained by relating the nucleic acid content of the product to that of the selected fungus grown in such a way as to be free of adhering substrate, for example as a surface culture on a solid medium or in aqueous medium followed by washing; and under growth conditions such as pH temperature and time as closely resembling those of the process as is practicable; and subsequently treating the fungus under similar conditions as are used in the process (e.g. de-naturation conditions). Allowance should also be made for any nucleic acid initially present in the unfermented substrate.

It has been found that a suitable textured product was achieved when the mycelial content, as estimated from the nucleic content of the product, having made allowance for the nuceic acids in the fermented substrate, reached a value of 40% by weight based on the total dry weight of the product. A better texture is achieved with a mycelial content of at least 45% and more preferably 50%.

Other methods, known to those skilled in the art, for determining mycelial content of the product may also be appropriate or may be developed as techniques improve for the isolation and measurement of small quantities of material such as chitin or other fungal components provided these are distinguishable from similar components in the initial substrate.

A heavy fungal growth is achieved by the inclusion in the substrate of a source of nitrogen assimilable by the fungus in a readily available form and also other growth promoting nutrients where necessary depending on the nature of the vegetable material and the type of fungus employed; by careful control of the range of particle sizes of the solid substrate components so that there are insufficient small particles to cause stickiness or compaction of the moist substrate with consequent limited access of air, a necessary requirement for fungal growth; and, by thorough cooking as above to achieve sufficient gelatinization of the starch so that it may be readily attacked by the fungus.

3. The fungal mycelium must be denatured after the heavy mycelial matrix has been formed and in such a way as to retain and strengthen the interwoven hyphal strands so as to form a firm, tough but chewy, fibrous, cohesive structure. This is most readily achieved by moist heat above 70° C. and preferably above 80° C., and more preferably at 100° C., but can also be achieved by treating with organic solvents and other known means of denaturing proteins. The abovementioned structure will be achieved directly unless the product dries out during denaturation in which case the dehydrated product will achieve such a structure after rehydration.

The fungus must be any non-toxic filamentous fungus capable of utilizing the carbohydrate substrate; preferably *Fungi Imperfecti*. Mucoraceous fungi such as those of the genus Rhizopus, and in particular *Rhizopus oligosporus* and *Rhizopus oryzae* are preferred because of their long-established usage in fermented foods such as tempeh; *Rhizopus stolonifer* and *Rhizopus arrhizus;* species of Mucor, Monilia and Neurospora; certain strains of the genus Aspergillus, in particular species used in Japanese fermented food products, such as *Aspergillus orgzae*, or *Aspergillus niger*. Agaricus, other species of edible mushroom Penicillium and Fusarium may also be used.

A variety of fermentable starch-based materials may be used either singly or in combination. Choice will probably be governed by economics and the desired product end use. The preferred starch sources are cereal grains, in particular barley, wheat, sorghym, oats, maize and rice. However, other starch sources such as cassave, sweet potatoes and the like may also be used.

The physical form of the fermentable starch-containing component of the substrate has a major influence on the texture of the end product. It is desirable, for a human food product with a pleasant mouth-feel, to remove fibre before fermentation, for example by decortication. This is not essential if the product is to be used for animal consumption. Of critical importance is the particle size of the moist substrate, which should present the greatest surface area per unit volume to facilitate mycelial growth and utilization of the substrate consistent with minimal compaction, to ensure adequate diffusion of air necessary for efficient mycelial growth on all particles. The particle size of the moist starch-containing component when ready for fermentation should be such that all overall dimensions are less than 3 mm. The preferred form has all overall dimensions between 0.5 and 3 and more preferably 1 and 2 mm. Too high a proportion of small particles may cause stickiness and/or compaction; thus if small particles, for example with all dimensions less than about 0.5 mm, are included they should be limited to less than 25%. Throughout this specifications and claims the statement "all overall dimensions are less than x mm", wherein x is any number as used herein is not intended to exclude the use of vegetable material some of the particles of which have larger dimensions as long as such large particles are not present in sufficient quantities to be substantially obviously visible in the fermented product.

In this specification and claims, the term "major interhyphal distance" is used to refer to a distance exceeding 0,5 mm between fungal mycelia in the product of the invention, caused by interstitial entrapped moisture, gas bubbles, substrate or substrate degradation products.

The assimilable nitrogen source may be proteinaceous or non-proteinaceous and should be present in such quantity as to allow synthesis of sufficient fungal mycelia to impart the desired texture as described above. This will depend on the efficiency of the conversion of the carbohydrate to fungal mass, as well as conversion of the nitrogen source to fungal protein. For example an increased fungal concentration can be achieved in the fermented product without further synthesis of fungal protein, simply by the fungus continuing to metabolize carbohydrate to carbon dioxide and other volatiles, thus reducing the overall mass of the end product.

Different fungi have different abilities to utilize the various inorganic nitrogen sources. Some nitrogen sources may be inhibitory at some concentrations but utilized at lower levels. In general, Aspergillus, Fusarium and Rhizopus will utilize a wide range of ammonium salts and meat; some will also utilize nitrates. In any case the nitrogen utilization pattern of a selected fungus can be readily determined by those skilled in the art.

All fungi will utilize other protein nitrogen or hydrolysis products thereof such as peptides, amino-acids and the like. Suitable sources of such proteinaceous nitrogen may include meat or fish particles, offal or by-product particles or meals; vegetable proteins such as soybeans, in the form of particles, meals or flours; protein extracts isolates or concentrates; casein or other milk products, including whey; single cell protein preparations such as yeast, yeast extracts concentrates or isolates; hydrolysates of the above; and the like.

Proteinaceous and non-proteinaceous nitrogen sources may be used singly or in combination.

The inclusion level of a particular protein containing material will depend on its nature and physical properties including particle size and texture. If added in small proportions as small particles, for example moist particles with all dimensions less than about 0.5 mm, the texture of the added protein containing material is not important. However, particle size is important in avoiding compaction of the moist substrate. If firm particles such as soybeans are included, the maximum dimension of the moist particles should be less than about 2.5 mm and preferably less than about 1.0 mm, otherwise the particles remain clearly visible in the final product and impart a granular appearance and texture uncharacteristic of meat.

The maximum inclusion level of larger particles of a protein-containing material will depend on its properties, in particular fermentability, and should be determined experimentally in each case. The determining criterion is that sufficient mycelium be formed to bind the residual substrate components into a firm matrix as previously described and that the residual particles are not substantially obvious in the product. Any mycelium formed through fermentation of the protein containing material will contribute to the mycelial content.

Other nutrients which improve mycelial growth may also be added in proportions appropriate to the requirements of the particular fungus used and can readily be determined. These may include phosphates, sulphates, salts of potassium, iron, magnesium, copper, zinc, calcium etc.

The moisture content of the compound substrate is of great importance; it should be sufficient to fulfil the water requirements of the fungus and to permit sufficient gelatinization of the starch so that it may be readily attacked by the fungus, yet the moisture content should not be so great as to allow excessive starch gelatinization which causes the particles to become sticky thus inhibiting adequate access of air. The optimum water content will differ for different substrates and must be determined experimantally in each case. It will usually fall in the range 45–70%, preferably 55–67% moisture. For cereal grains the optimum moisture level is usually between 50–67%, for example, the preferred moisture content for wheat and pearled barley particles is about 60%.

The method of preparation of the moist compound substrate should be such as to ensure uniform gelatinization of the starch and formation of discrete starch-containing particles, while avoiding excessive local gelatinization of the starch. This can be achieved with ground grain particles, by stirring the dry ingredients while adding the required quantity of hot water which may contain the soluble nutrients, and continuing to mix while cooking the substrate at a temperature above the gelatinization temperature of the selected starch source, until the moisutre has penetrated and gelatinization has occured through the starch-containing particle. A satisfactory degree of gelatinization can be achieved for example with particles of pearled barley at a moisture content between 55–60% by heating with frequent stirring at 90° C. for 30 minutes.

Although sterilization of the substrate and subsequent aseptic processing are desirable in the context of preparation of a food substance, they are not essential features of the process. If required, sterilization can be achieved either by presterilising the ingredients separately before mixing and cooking, for example by dry heat sterilization of the solid consittuents and by autoclaving or sterile filtration of an aqueous solution of the soluble components; or by heating the moist substrate at an appropriate temperature and for sufficient time to achieve simultaneous sterilization and cooking, for example, at 15 psig steam pressure for 15–60 minutes.

Control of pH during fermentation of moist solid substrates is difficult to achieve by addition of acid or alkali, but does not appear to be critical within the range 4–8 for most fungi. Some degree of buffering is provided by the substrate, but in general little control over the pH can be achieved during fermentation. The initial pH of the medium will depend on the optimum growth pH and tolerance of the process organism but will normally lie between 4 and 5.5. Below pH4 there is an increasing tendency towards starch hydrolysis during cooking; between 5.5 and 8 there is an increasing susceptibility to infection when using non-aseptic conditions.

The fermentation may be carried out according to any of the methods described in the literature for moist solid fermentations, such as in trays or perforated plastic bags. Maintenance of a high relative humidity, preferably above 90% and more preferably above 95% is desirable to prevent drying of the substrate and to retard sporulation; both of which factors detrimentally affect the appearance and quality of the product. The temperature of fermentation should be maintained as close as possible to the optimum growth temperature of the process organism, which can be determined experimentally. An adequate supply of oxygen to the fungus is essential for heavy growth.

After a suitable growth period, which will vary with the organism and conditions used, it will be found that much of the starch substrate has been converted to a dense matrix of fungal mycelia interwoven around and through all spaces containing residual substrate material, and low power microscopic examination will show that the mycelia have substantially penetrated the spaces originally occupied by the starch-based substrate particles. It has been found with Rhizopus oligosporus grown on barley with ammonium lactate, (6% of total substrate (dry basis)) or soybeans (25% of total substrate (dry basis)) as the nitrogen source, that the desired texture is achieved when the total content of acid-hydrolysable starch and starch degradation products has fallen below 45%, preferably below 40% and more preferably below 35% of the fermented material. The acid-hydrolysable starch may be measured by any suitable procedure such as homogenizing the material with 2 N HCl and heating at 100° C. for 2–3 hours to hydrolyze the starch, partially neutralizing the hydrosylate, diluting and filtering, then assaying for reducing sugar by any standard method, for example as in "Official Methods of Analysis of the AOAC" pp532–533 (11th edition 1970).

The nucleic acid content of such a product was found to be between 2.5% and 3% of the fermented material (dry basis). Allowance was made in these values for nucleic acids initially present in the unfermented substrate.

A control substrate-free mycelial preparation prepared on aqueous medium between 5–6% nucleic acid. Thus it is estimated that the fermented product contained between 40% and 60% mycelium on a dry basis. This material is firm, rather brittle and has no resemblance to meat; however, after denaturation of the protein-containing mycelium, for example by heating in water, the material develops a firm, chewy consistency, and when minced or diced has an appearance and texture resembling meat, or if dried during denaturation achieves these characteristics after rehydration. Denaturation can be achieved by heating either in the presence only of that water already present in the product or in the presence of additional water or aqueous solutions or suspensions or in oil or fats at a temperature preferably above about 70° C. and more preferably above 100° C. until the material develops the above characteristics; by treating with organic water-miscible organic solvents of the type normally used in food processing; or by certain other known methods of denaturing proteins. The preferred method is to boil in water or aqueous solutions or suspensions. The time and temperature required will depend on the size and shape of the fermented material pieces, on the nature and concentration of the dissolved or suspended components, and the pH of the solution or suspension. Preferably the fermented material is minced, sliced or cut into chunks and heated in water or sodium chloride solution, or solution containing suitable flavourings, at 15 psig (121° C.) for 5 to 10 minutes, or boiled at atmospheric pressure for 10 to 20 minutes. The denatured material may suffer some loss in soluble components during denaturation, particularly if this is effected in aqueous solutions. This does not significantly affect the proportions of acid-hydrolysable starch and mycelium in the product. However, it has been found that the nucleic acid content of the product may be affected during denaturation, and it is emphasized that if this method of estimation of fungal mycelium is used, then it is important that the substrate-free mycelial standard used for measurement of nucleic acid content be treated in the same way as the product.

Nucleic acids may be reduced before or during the denaturation step. The denatured material, rehydrated if dried during denaturation, may be incorporated directly into prepared foods such as stews and minces or into petfood preparations and may be canned without loss of texture.

The meatlike material may be dried by an appropriate meethod such as dry heating, heating under reduced pressure, freeze drying, or by direct evaporation of solvent treated material. For example a minced product can be dried in a forced draught oven at 50°–80° C. to yield a hard brown irregular particle which rehydrates to a form closely resembling cooked minced lean beef. After rehydration it may be combined with minced beef, port, chicken or other meats and used in savoury mince and other prepared meat dishes such as patties, hamburges, sausages, pies, or it may be flavoured or used along.

The following examples illustrate the invention but should not be construed as limiting on the appended claims. All parts and percentages expressed are by weight unless otherwise stated. Temperatures are degrees celsius.

EXAMPLE 1 i. Substrate preparation

A nutrient solution was prepared containing the following in 1175 ml. water: Urea (34 g); $KH_2PO_4$ (15 g); $(NH_4)_2HPO_4$ (3.7 g); $MgSO_4.7H_2$) (10 g); $CaCl_2.2H_2O$ (5.3 g); $(NH_4)_2SO_4$ (3.3 g); sodium citrate. $2H_2O$ (7.0 g); $CuSO_4 5H_2O$ (0.08 g); $FeSO_4.7H_2O$ (0.44 g). This solution was heated and added to 1100 g of ground wheat (10% moisture) graded such that all particles passed through a 12 mesh/inch (Tyler Standard Screen Scale) screen but were retained by a 14 mesh/inch screen. The mixture was heated by immersion of the container in a boiling water bath and was cooked with stirring for 20 minutes, by which time all of the solution was absorbed. Meatmeal (250 g, 7% moisture) was added and stirred into the moist grain mixture, followed by a further 250 ml. of water. The moisture content of the final mixture was approximately 55%. The average size of the wheat particles after cooking was 1.0–2.0 mm maximum dimension.

The mixture was distributed in 25 cm diameter×7 cm deep aluminium trays to a depth of about 2.5 cm, covered with aluminium foil and autoclaved at 15 psig steam pressure for 30 minutes. After cooling, each tray was inocluated aseptically with 10 ml. of a heavy spore suspension of *Rhizopus oligosporus* in water. The spores were produced on an agar mediium containing, by weight (NH$_4$)$_2$SO$_4$ (0.72%); Na$_2$HPO$_4$ (0.16%); KH$_2$PO$_4$ (0.19%); cassava flour (0.1%); agar (0.15%). After inoculation the substrate was stirred well aseptically, covered with foil, and incubated in a humidified incubator at 32° C. for 60 hours. By this time the substrate was heavily grown with fungal mycelium.

ii. Processing of the fermented material

A portion of the fermented material (400 g moist wet) was cut into 1–2 cm cubes and boiled for 10 minutes in 600 gm of a gravy containing, by weight, cornflour (10%); peanut oil (6%); glycerol monostearate (0.06%); sodium chloride (2%); beef flavouring (Saroline 38-2919, Bush Boake & Allen, 2%) sugar 1%. The cooked material was preserved by dispensing into 500 g jars and sterilizing by autoclaving at 15 psig for 95 minutes.

The product was midbrown in colour, consisting of firm, elastic meatlike chunks in a thick gravy. Although the chunks had a fibrous mouthfeel to humans, it was found to be readily accepted by dogs.

EXAMPLE 2 i. Substrate preparation

A nutrient solution was prepared containing the following in 1 liter of water: KH$_2$PO$_4$ (15 g); (NH$_4$)$_2$HPO$_4$ (3.7 g); MgSO$_4$.7H$_2$O (10 g); (MH$_4$)$_2$SO$_4$ (3.3 g); citric acid (5 g); CuSO$_4$.5H$_2$O (0.08 g); FeSO$_4$.7h$_2$O (0.44 g); ammonium lactate (120 g of 50% w/v solution). A separate solution of CaCl$_2$.2H$_2$O (5.3 g) in 400 ml. of wter was prepared. The two solutions were sterilized separately by autoclaving at 15 psig for 15 minutes.

Ground pearled barley, graded as in Example 1, (1100 g, 10% moisture); meatmeal (100 g 7% moisture); soymeal (100 g 7% moisture), were mixed dry and sterilized in 5 mm deep layers by dry heat at 150° C. for 1¾ hours, then transferred to a sterilized cooking vessel fitted with a lid. The hot nutrient solutions were added with stirring and the cooking vessel placed in a boiling water bath. The mixture was stirred at frequent intervals for 45 minutes. All liquid was absorbed within 5 minutes, but further cooking with stirring was required to ensure complete penetration of water and nutrients into the grain particles and to achieve the desired degree of gelatinization of the starch. The moisture content after cooking was approximately 57%. The size of the cooked grain particles varied between 0.5 and 2.5 mm diameter. After cooling, the moist substrate was inoculated with 100 ml of a heavy spore suspension of *Rhizopus oligosporus,* stirred well and distributed into clean plastic bags (15 cm × 30 cm flat) perforated at 0.5 cm intervals. The depth of the substrate was 2.5–3 cm. The bags were incubated in a well aerated humidified cabinet at 32° C. for 60 hours.

ii. Processing of the fermented material

The fermented blocks were cut into 1–2 cm cubes and placed in sufficient boiling water to barely cover the cubes (approximately 1 liter of water per kg moist weight of cubes), and boiled for 15 minutes. This water was then used in the preparation of a gravy of the following composition, by weight: beef dripping (4.5%); fresh onion (3.3% wet weight); plain flour (5.8%); ground fresh ox liver (8.7% wet weight; salt (1.5%); monosodium glutamate (0.1%); caramel colouring (0.7%); meatmeal (3.5%); glycerol monostearate (0.5%) Vitamin A/D$_3$ (Roche 500/100,) (0.55 mg %). The boiled cubes were added to the gravy in the ratio 40:60 by weight, based on the moist weight of the fermented material before boiling. The petfood was canned in 30 ml volume cans, sterilized by autoclaving at 15 psig for 1 hour.

The canned material had the appearance of discrete chunks of meat in a thick gravy with a marked odour of liver. It provided a balanced formulation of the basic essential nutrient requirements for dogs, and was found to be readily accepted by dogs. A typical analysis of the canned product is as follows: (moist basis) crude protein (N×6.25)7.5%, fat, 3%, fibre, 0.5%; sodium chloride, 1%.

EXAMPLE 3

Human food (Barley based)

Substrate preparation

Nutrient salt solutions were prepared and sterilised as in Example B with the exception that the ammonium lactate was replaced by lactic acid (75 ml of 50% w/v solution). and NH$_4$OH (45 ml of 28% w/v solution). Ground pearl barley (1100 g) and soyflour (all particles passing through a 16 mesh/inch sieve) prepared from whole soybeans (200 gm, 10% moisture) were mixed and sterilized by dry heat, cooked with the nutrient salts solutions, cooled, incoluated and incubated as in Example 2.

ii. Processing

The fermented material was minced in a domestic meat grinder using a medium plate. The minced material was treated twice with 3 volumes of 3% sodium chloride solution for 10 minutes. The cooked minced material was drained and further water expressed by squeezing through cheesecloth until the moisture content of the material was reduced to approximately 70%.

This material resembled cooked minced lean beef in texture and colour, and had a slightly salty flavour. It could be substituted for a proportion of fresh minced beef in a variety of dishes as illustrated by the following examples.

(a) Canned savoury mince

Textured minced material prepared as described (1 kg) was mixed with fresh minced beef (500 gm), fried briefly and heated in a gravy containing fried onion (100 gm fresh); beef dripping (100 gm); plain flour (100 gm); beef flavouring (Bonox, Kraft Foods, (10 gm)); caramel colouring (5 gm); salt (1.6 gm) in approximately 1.2 liters of water. This preparation was preserved by canning in 300 ml volume cans, sterilized by autoclaving a 15 psig for 1 hour.

The canned products had an appearance, texture and flavour very similar to an all beef mince preparation, with the added advantage that the material maintained its firm texture after autoclaving (b) Bolognaise sauce The textured material prepared in Example (a) was used in the preparation of bolognaise sauce, and was found to be indistinguishable in flavour and texutre from an equivalent all beef preparation.

(c) Hamburger

The material obtained after heating the minced fermented product in sodium chloride solution and reducing the moisutre content to 70% was mixed with an equal weight of fresh minced beef (moisture content 70%), seasoned with salt and pepper and fried in flat rounds, as hamburgers. The product had the flavour and consistency of a good quality hamburger.

EXAMPLE 4

The textured protein-containing material was prepared as in Example 3 except that after boiling in sodium chloride solution, the expressed material was extracted three times in 2 volumes of acetone. After the last extraction the material was drained to remove as much acetone as possible and air dried at room temperature.

The product so prepared consisted of whitish flakes and virtually no odour or flavour. The protein content (Nx 6.25) was approximately 43% (dry basis). The flakes rehydrated rapidly on addition of water, and at a moisture content of between 70–75% resembled cooked minced beef in colour, texture and chewiness. When combined with fresh minced beef in the ratio of 2 parts of product to 1 part of beef, it could be used in the preparation of meat pies, hamburgers, bolognaise sauce, and other similar dishes, which were found to be indistinguishable for similar all meat products.

EXAMPLE 5

Fermented material was prepared as in Example 3. The fermented material was minced and treated three times with 3 volumes of iso-propyl alcohol per volume of wet material drained and washed three times in water to remove residual solvent. The water was drained and the solids expressed until the moisture content was reduced to 70%. This material resembled cooked minced beef in colour, and texture and had a slight, bland flavour.

EXAMPLE 6

Human food, acetone denatured, air dried

Fermented material was prepared as in Example 3, minced and treated three times with 3 volumes of acetone per volume of moist minced material, drained and air dried at 25° C. in forced draught to remove acetone. When suspended in warm (40° C.) water the material rehydrated rapidly to give a chewy product resembling cooked lean meat in colour and texture, with a bland flavour. It is important to remove all traces of solvent from the material or the flavour is adversely affected.

EXAMPLE 7

Fermented material was prepared as in Example 3 with the exception that instead of fine soybean particles the substrate contained 25% of ground soybeans graded so as to pass through a 14 mesh/inch sieve but be retained by a 16 mesh/inch sieve. The fermented material (100 gm moist) was moistened with 10 ml water, minced and dried at 80° C. in a forced draught oven for 6 hours. The dry product was brown and brittle. On rehydration by soaking in warm water (40° C.) containing 3% sodium chloride, the material resembled cooked lean beef in colour and texture and had a flavour resembling yeast extract.

EXAMPLE 8

Fermented material was prepared as in Example 7. The fermented material (100 gm moist) was moistened with 10 ml of a 10% solution of beef flavouring (Bonox; Kraft Foods Ltd.) minced, and dried at 80° C. for 6 hours. The product was similar in properties to that described in Example G, but with a stronger flavour.

EXAMPLE 9

Fermented material was prepared as in Example 3 except the barley was replaced by ground maize of similar particle size. The material was minced and boiled in 3 volumes of 3% sodium chloride solution per volume of minced moist material. After draining and expressing excess moisture so that the product retained about 65% moisture, the materials had a firm chewy texture and bland, slightly nutty flavour and a pale brown colour.

EXAMPLE 10

Ground pearled barley graded as in Example 1 (80 g, 10% moisture) was sterilized by heating in a hot air oven at 150° C. for 60 minutes. Fresh minced beef (70 g, 70% moisture) was added to 124 ml of a solution containing $KH_2PO_4$ (1.5 g); $(NH_4)_2HPO_4$ (0.37 g); $MgSO_4.7H_2O$ (1.0 g); $(NH_4)_2SO_4$ (0.33 g); citric acid (0.5 g); $CuSO_4.5H_2O$ (0.008 g); $FeSO_4.7H_2O$ (0.04 g); $CaCl_2$ (0.53 g); lactic acid (7.5 ml of 80% w/v solution); $NH_4OH$ (4.5 ml of 28% w/v solution). The meat and nutrients solution were sterilized by autoclaving at 15 psig for 15 minutes, then added with stirring to the hot grain in a cooking vessel which was placed in a boiling water bath. The mixture was stirred at frequent intervals while cooking for 30 minutes. The moisture content after cooking was approximately 65%. After cooling, the moist substrate was inoculated with 10 ml of a heavy spore suspension of *Rhizopus oligosporus*, mixed well and distributed in perforated plastic bags to a depth of about 2.5 cm. The bags were incubated in a well aerated humidified cabinet at 32° C. for 63 hours.

The fermented material was minced and boiled for 20 minutes in 3 volumes of 3% sodium chloride solution per volume of moist minced material. The final product resembled cooked minced beef in appearance and texture and the added meat particles were visually indistinguishable from the other material.

Cubes of fermented material (approximately 1 cm cubes) were similarly treated. The heated and drained product was similar to diced meat in appearance and texture, and had a bland flavour.

EXAMPLE 11

Fermented material was prepared as in Example 3 with the exception that no soyflour was included. The fermented material was cut into 1–2 cm cubes or minced, and boiled in 3% sodium chloride solution for 20 minutes. The product was lighter in colour than comparable products with included soy protein or meat, but was similar in texture and appearance.

EXAMPLE 12

Barley-based, soybean added, no non-protein nitrogen

Around pearled barley (75 gm) graded between 12–16 mesh and ground soybeans (25 g) graded between 14–16 mesh, were cooked in approximately, 125 ml water with frequent stirring for 30 minutes, fresh water being added as necessary to maintain the moisture content at about 58%. After cooling, the substrate was inoculated with a spore suspension of *Rhizopus oligosporus*, distributed in perforated plastic bags to a depth of 25 mm and incubated at 32° C. When sampled after 24 hours the acid-hydrolysable starch was about 53% of the total matter, dry basis, and the nucleic acids had increased from 1.4 to 3.2% an increase of 1.8%. The texture of the material after boiling was soft, starchy and rather grannular. Further incubation for a total of 48 hours yielded a product containing about 33% acid-hydrolysable carbohydrate, the nucleic acid content having risen to 4.1%, an increase of 2.7%. This material on denaturing by boiling in water for 15 minutes provided a product of chewy, resilient consistency, which when minced closely resembled minced meat. Observation under a low power (plate) microscope showed closely packed areas of mycelia surrounding spaces of approximately 1–2 mm maximum diameter. Often with some mycelia growing more loosely through the space. Spaces containing discrete particles of material, presumably soybean particles, were also visible.

EXAMPLE 13

Fermented material was prepared as in Example 3, but using dried cassave chips of similar particle size (400 g), graded ground soybeans of the same particle size (95 g) and soyflour (25 g) and excluding the ammonium lactate solution. The material was sliced into 1–2 cm cubes and boiled for 15 minutes, minced and dried in a forced draught oven at 70° C. overnight. The dry product was dark brown, with the lighter coloured fibrous matter evident. On rehydration by boiling in 2% NaCl, the material closely resembled cooked mincemeat in colour and texture and possessed a bland flavour.

EXAMPLE 14

A substrate was prepared as an Example 12. After cooling the substrate was inoculated with a spore suspension of *Aspergillus oryzae*, distributed in perforated plastic bags to a depth of 25 mm and incubated at 30° for a period of 3 days. The product was boiled in water, minced and dried at 80° C. in a hot-air oven. Upon rehydration to approximately 65% by weight of moisture, the product had a firm chewy texture with an appearance resembling that of mince meat.

Although the product of the invention is able to be produced as described herein, the disclosure of this specification should not be construed so as to imply that products so produced will necessarily be acceptable under any particular legislation relating to foodstuffs for human and/or animal consumption.

What we claim is:

1. In a process for preparing a protein-containing product by cultivating an amylolytic fungus on a solid substrate comprising a solid carbohydrate source and a nitrogen source, the improvement which comprises the steps of:
   (a) providing a particulate starch-based material which does or does not include a nitrogen source;
   (b) partially gelatinizing the starch component of said material in the presence of water to a particulate substrate composed of particles of which a predominant proportion have a particle size wherein the overall dimension is within the range of 0.5 mm to 3 mm, with the proviso that particles of larger dimensions are not present in sufficient quantity to be substantially visible in the fermented product;
   (c) adding a nitrogen source if the nitrogen source in step (a) is absent or insufficient, before, during or after step (b) whilst maintaining the physical state of said substrate;
   (d) inoculating said substrate with at least one amylolytic fungal strain;
   (e) incubating said inoculated substrate in the presence of oxygen and moisture until substantially all particles of the starch-based material are substantially degraded to a non-particulate form and the spaces originally occupied by the starch-based substrate particles and containing the starch degradation products are closely bound together by a network of mycelia; and
   (f) denaturing the products of steps (e) wherein said nitrogen source is assimilable by said fungal strain(s), and is present in a total amount which is non-inhibitory and sufficient to allow adequate mycelial growth in step (e), and, if said nitrogen source is particulate, the predominant proportion has a particle size wherein the overall dimension is less than 2.5 mm with the proviso that particles of larger dimensions are not present in sufficient quantity to be substantially visible in the fermented product.

2. The process as claimed in claim 1 wherein said starch-based material is at least one cereal grain.

3. A process as claimed in claim 2 wherein said cereal grain is decorticated.

4. A process as claimed in claim 1 wherein said starch-based material is at least one of the solanaceous starches or sago.

5. A process as claimed in claim 1, wherein the substrate particles have overall dimensions within the range of 1 mm to 2 mm.

6. A process as claimed in claim 1, wherein said substrate has a moisture content before step (e) of 45 to 70% by weight.

7. A process as claimed in claim 1 wherein said nitrogen source is a proteinaceous nitrogen source.

8. A process as claimed in claim 1 wherein said nitrogen source is a non-proteinaceous nitrogen source.

9. A process as claimed in claim 1 wherein said nitrogen source is particulate, the particles of said nitrogen source having all overall dimensions less than 1 mm (as hereinbefore defined).

10. A process as claimed in claim 1 wherein said fungal strain is a member of the class, *Fungi Imperfecti*.

11. A process as claimed in claim 10 wherein said fungal strain is a mucoraceous fungus.

12. A process as claimed in claim 11 wherein said fungal strain is a member of the genus, Rhizopus.

13. A process as claimed in claim 12 wherein said fungal strain is *Rhizopus oligosporus*.

14. A process as claimed in claim 1 wherein said fungal strain is a member of the genera, Aspergillus, Penicillium or Fusarium.

15. A process as claimed in claim 1 wherein said fungal strain is a member of the genus Agaricus or other edible mushroom species.

16. A process as claimed in claim 1 wherein aseptic processing techniques are used.

17. A process as claimed in claim 1 wherein said inoculated substrate is incubated in the presence of humidified air.

18. A process as claimed in claim 17 wherein said humidified air has a relative humidity greater than 90%.

19. A process as claimed in claim 18 wherein said relative humidity is greater then 95%.

20. A process as claimed in claim 1 wherein said inoculated substrate is incubated until the acid hydrolysable starch and starch degradation products content has fallen below 45% by weight based on the weight of the total mass produced in step (e) (dry basis).

21. A process as claimed in claim 20 wherein said content has fallen below 40%.

22. A process as claimed in claim 20 wherein said content has fallen below 35%.

23. A process as claimed in claim 1, wherein the mycelial content of said incubated inoculated substrate, before denaturation, has reached a minimum of 40% by weight based on the weight of total mass produced in step (e) (day basis).

24. A process as claimed in claim 23 wherein the mycelial content has reached a minimum of 45%.

25. A process as claimed in claim 23, wherein the mycelial content has reached a minimum of 50%.

26. A process as claimed in claim 1 wherein the product of step (e) is denatured in an aqueous medium at a temperature exceeding 70° C.

27. A process as claimed in claim 1 wherein the product of step (e) is denatured in at least one oil and/or fat at a temperature exceeding 100° C.

28. A process as claimed in claim 1 further comprising one or more of the steps:
   (g) mincing or cubing the product of step (f);
   (h) adding flavouring materials to the product of, or during, step (f);
   (i) dehydrating the product of any one of steps (f), (g) or (h); and
   (j) reducing the nucleic acid content of the product of step (e) before, during or subsequent to step (f).

29. The product of the process of claim 1.

* * * * *

UNITED STATES PATENT AND TRADEMARK OFFICE
CERTIFICATE OF CORRECTION

PATENT NO. : 4265915

DATED : May 5, 1981

INVENTOR(S) : Mary E. MacLennan & Martial Lawson

It is certified that error appears in the above—identified patent and that said Letters Patent is hereby corrected as shown below:

Claim 11, line 1: change "10" to "1".

Signed and Sealed this

Seventh Day of September 1982

[SEAL]

Attest:

Attesting Officer

GERALD J. MOSSINGHOFF

Commissioner of Patents and Trademarks

Disclaimer 4,265,915.—*Mary E. MacLennan* and *Martial Lawson*, New South Wales, Australia. PROTEIN-CONTAINING FOOD MATERIAL. Patent dated May 5, 1981. Disclaimer filed Sept. 9, 1982, by the assignee, *Bioenterprises Pty. Ltd.*

Hereby enters this disclaimer to claim 29 of said patent.
[*Official Gazette October 26, 1982.*]